(12) United States Patent
Biondi et al.

(10) Patent No.: US 6,839,753 B2
(45) Date of Patent: Jan. 4, 2005

(54) NETWORK MONITORING SYSTEMS FOR MEDICAL DEVICES

(75) Inventors: James W. Biondi, North Haven, CT (US); Aaron Fand, Cheshire, CT (US)

(73) Assignee: Cardiopulmonary Corporation, Milford, CT (US)

( * ) Notice: Subject to any disclaimer, the term of this patent is extended or adjusted under 35 U.S.C. 154(b) by 672 days.

(21) Appl. No.: 09/791,334

(22) Filed: Feb. 23, 2001

(65) Prior Publication Data

US 2002/0120676 A1 Aug. 29, 2002

(51) Int. Cl.[7] .................................................. G06F 15/173
(52) U.S. Cl. ........................ 709/224; 709/203; 707/10
(58) Field of Search ................................. 709/224, 203; 707/10, 100, 104

(56) References Cited

U.S. PATENT DOCUMENTS

| | | | |
|---|---|---|---|
| 4,163,218 A | 7/1979 | Wu ........................ 340/310 A |
| 4,333,002 A | 6/1982 | Kozak ........................ 219/321 |
| 4,371,932 A | 2/1983 | Dinwiddie, Jr. et al. .... 364/200 |
| H727 H | 1/1990 | Pax ........................ 364/413.05 |
| 4,915,450 A | 4/1990 | Cooper ........................ 297/423 |
| 4,958,645 A | * 9/1990 | Cadell et al. ................ 600/484 |
| 4,972,314 A | 11/1990 | Getzinger et al. .......... 364/200 |
| 5,002,060 A | 3/1991 | Nedivi ........................ 128/671 |
| 5,003,984 A | * 4/1991 | Muraki et al. ............... 600/523 |
| 5,023,823 A | 6/1991 | Cargin, Jr. et al. ......... 364/708 |
| 5,049,873 A | 9/1991 | Robins et al. .......... 340/825.06 |
| 5,056,864 A | 10/1991 | Cooper ........................ 297/188 |
| 5,238,001 A | 8/1993 | Gallant et al. ............... 128/700 |
| 5,319,355 A | 6/1994 | Russek ........................ 340/573 |
| 5,319,363 A | 6/1994 | Welch et al. .......... 340/825.36 |
| 5,386,532 A | 1/1995 | Sodos ........................ 395/425 |
| 5,441,047 A | 8/1995 | David et al. ................ 128/670 |
| 5,452,356 A | * 9/1995 | Albert ........................ 380/271 |
| 5,481,255 A | * 1/1996 | Albert et al. ............... 340/7.21 |
| 5,482,050 A | 1/1996 | Smokoff et al. ............ 128/710 |
| 5,491,796 A | 2/1996 | Wanderer et al. ....... 395/200.09 |
| 5,511,553 A | 4/1996 | Segalowitz .................. 128/696 |
| 5,673,692 A | 10/1997 | Schulze et al. ............. 128/633 |
| 5,685,314 A | 11/1997 | Geheb et al. ................ 128/700 |
| 5,687,717 A | 11/1997 | Halpern et al. ............. 128/630 |
| 5,923,557 A | 7/1999 | Eidson ................... 364/471.03 |
| 5,944,659 A | * 8/1999 | Flach et al. .................. 600/300 |
| 5,960,403 A | 9/1999 | Brown ........................... 705/2 |
| 5,974,463 A | 10/1999 | Warrier et al. .............. 709/225 |
| 5,987,519 A | 11/1999 | Peifer et al. ................. 709/230 |
| 6,104,333 A | 8/2000 | Wood, Jr. .................... 341/173 |
| 6,112,194 A | 8/2000 | Bigus .......................... 706/11 |
| 6,122,639 A | 9/2000 | Babu et al. .................. 707/103 |
| 6,128,371 A | 10/2000 | Hazama ....................... 379/32 |
| 6,151,308 A | 11/2000 | Ibanez-Meier et al. ..... 370/316 |
| 6,158,430 A | 12/2000 | Pfeiffer et al. ......... 128/202.27 |
| 6,213,954 B1 | * 4/2001 | Chen .......................... 600/500 |
| 6,402,691 B1 | * 6/2002 | Peddicord et al. .......... 600/300 |
| 6,408,330 B1 | * 6/2002 | DeLaHuerga ............... 709/217 |
| 6,589,170 B1 | * 7/2003 | Flach et al. .................. 600/300 |
| 6,618,709 B1 | * 9/2003 | Sneeringer .................. 705/412 |

FOREIGN PATENT DOCUMENTS

| | | | |
|---|---|---|---|
| WO | 98/29790 | 7/1998 | |
| WO | 00/40145 | 7/2000 | |
| WO | 00/60522 | 10/2000 | |
| WO | 01/13190 A1 | 2/2001 | ........... G05B/19/42 |

OTHER PUBLICATIONS

International Searching Authority, "International Search Report", PCT Application No. PCT/US02/04515, mailed on May, 8, 2003, 4 pgs.

* cited by examiner

*Primary Examiner*—Mehmet B. Geckil
(74) *Attorney, Agent, or Firm*—Testa, Hurwitz & Thibeault, LLP

(57) ABSTRACT

A ventilator monitoring system is described for monitoring a plurality of ventilators. In one embodiment, a server including a dedicated ventilator application program for each type of ventilator, monitors a plurality of heterogeneous ventilators over a wireless network.

16 Claims, 13 Drawing Sheets

Figure 4. Listen Thread Flowchart
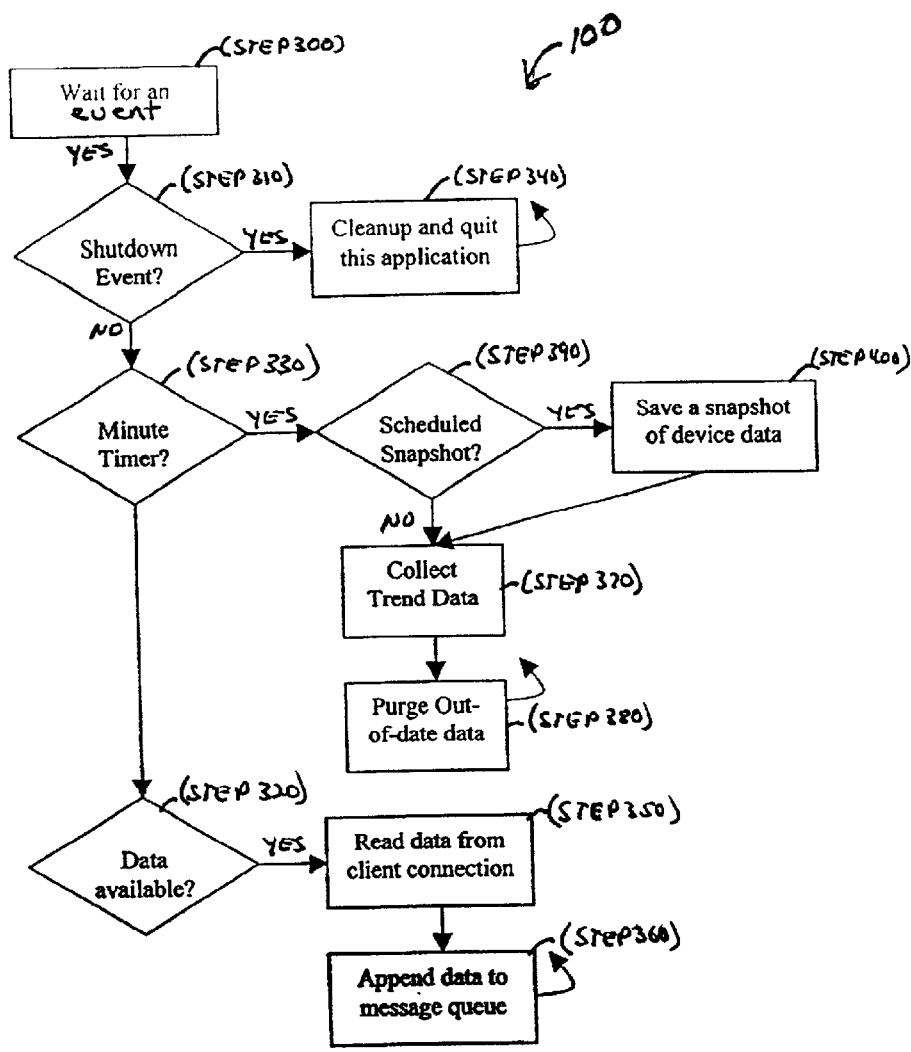

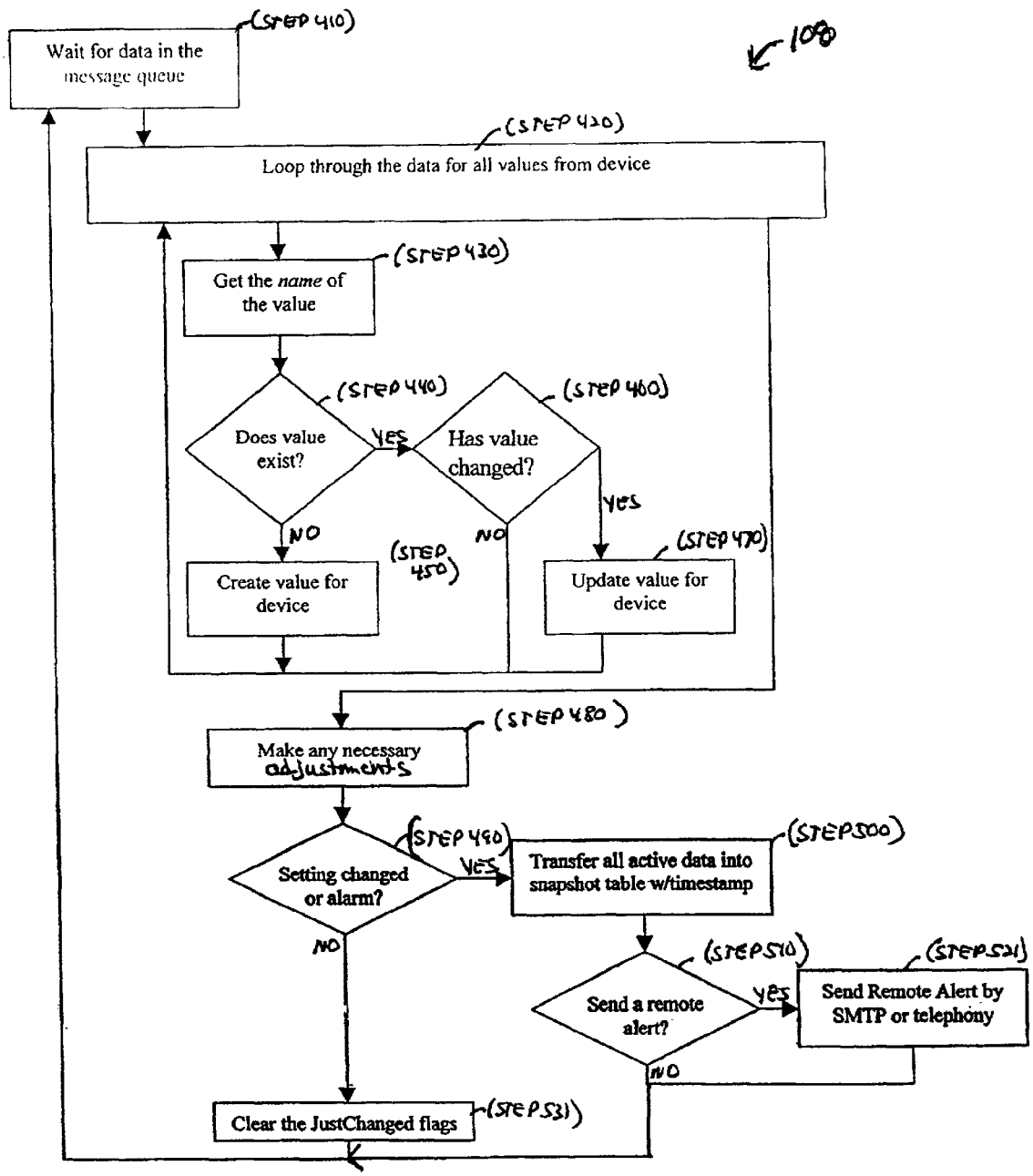
Figure 5 Load Thread Flowchart

Figure 6. Parsing Example
Return ("500 020 030 004"). The name of the each value is determined for loading into the active data table of the database. The above example might contain a tidal volume, oxygen setting, a high pressure limit and a inspiration time with the following database names: chTV, stFIO2, stPPAWhi, stITIME.
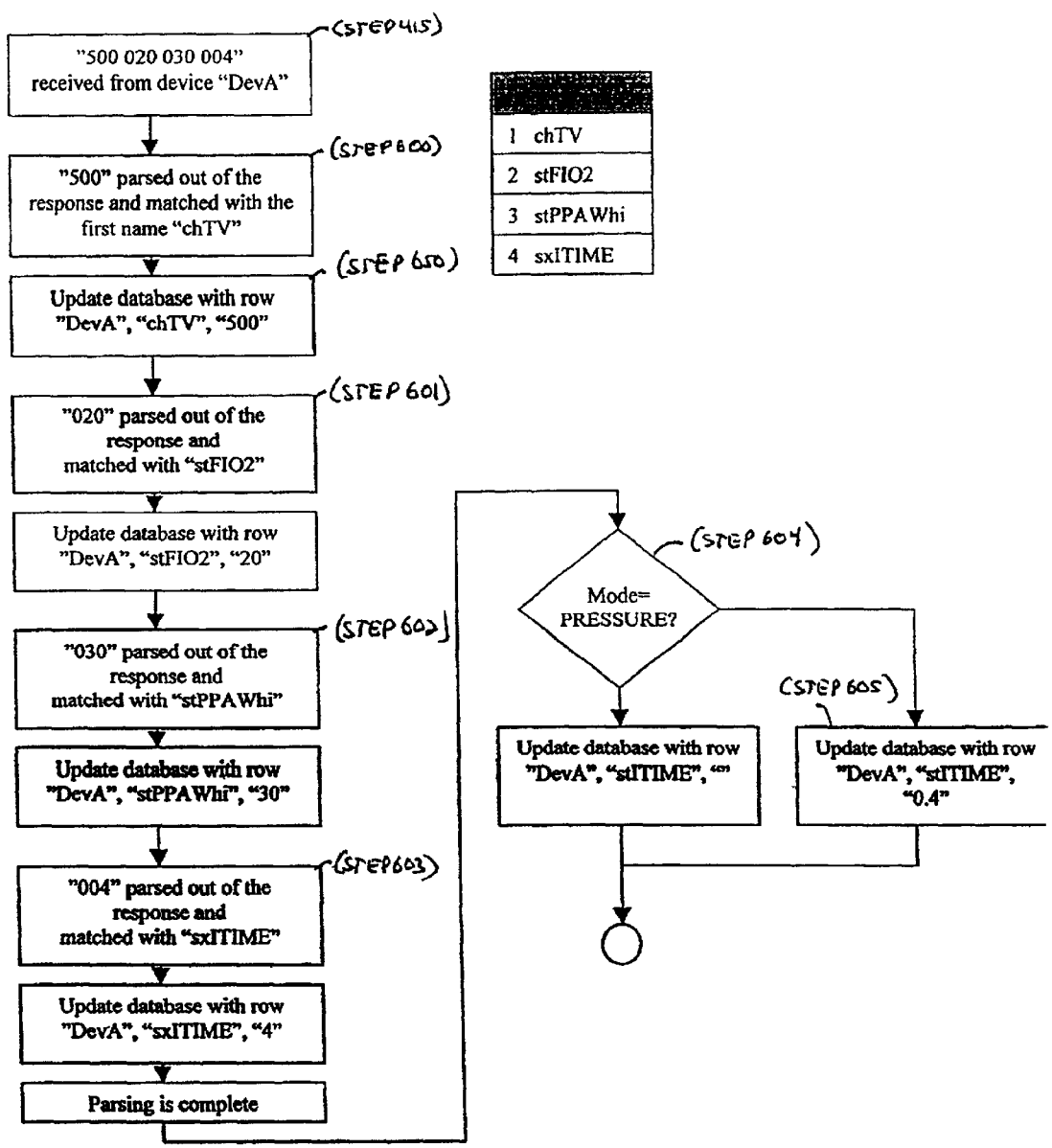

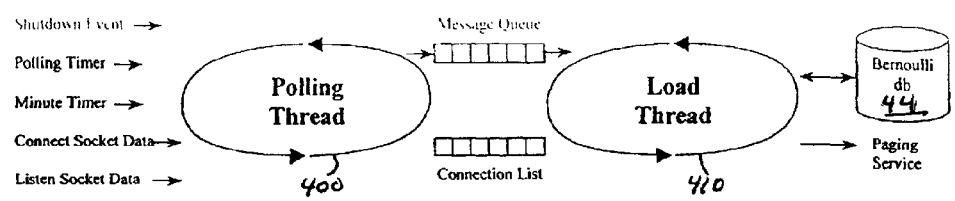
Figure 7: Generic Pollster Architecture

Fig 8 Polling Thread Flowchart
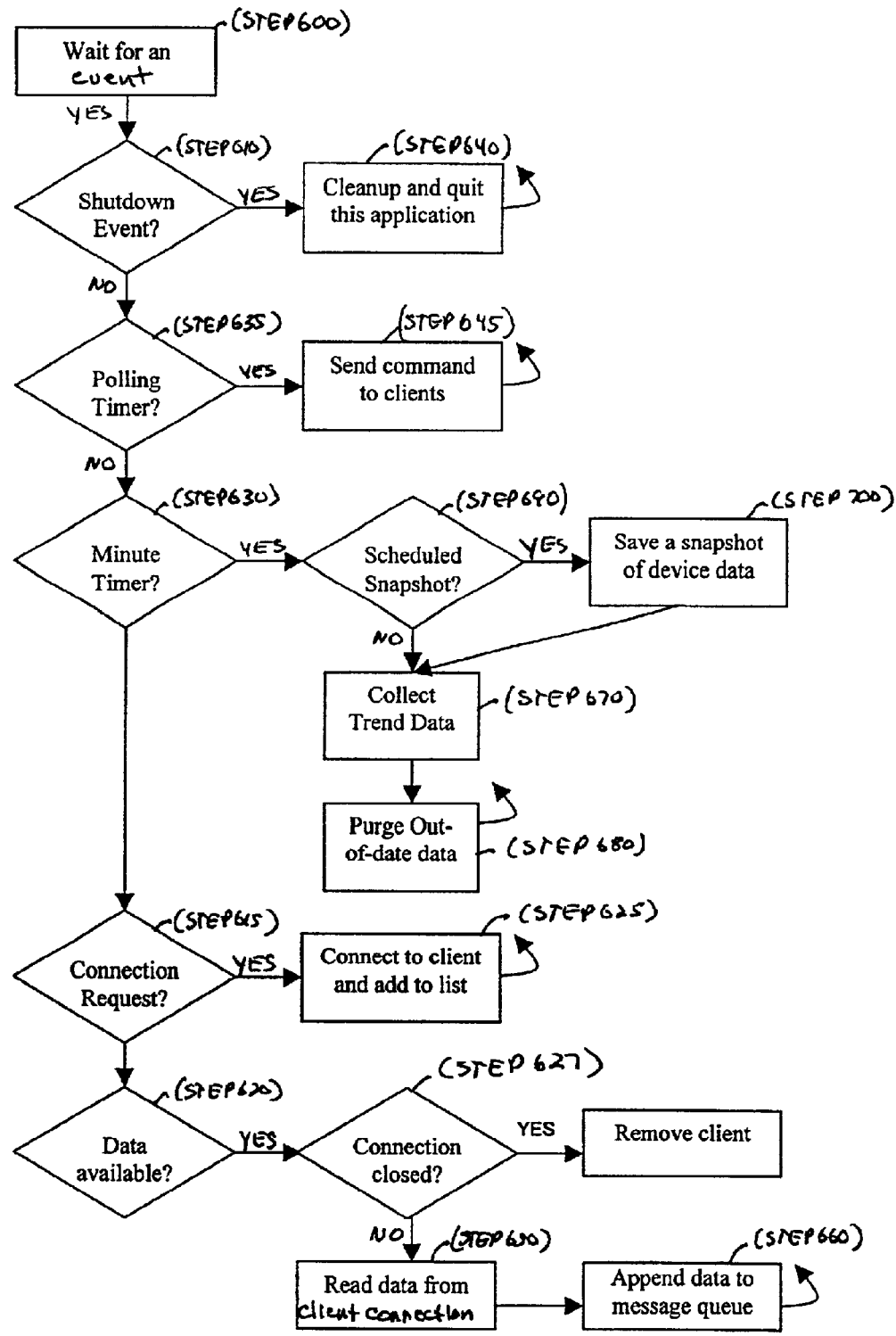

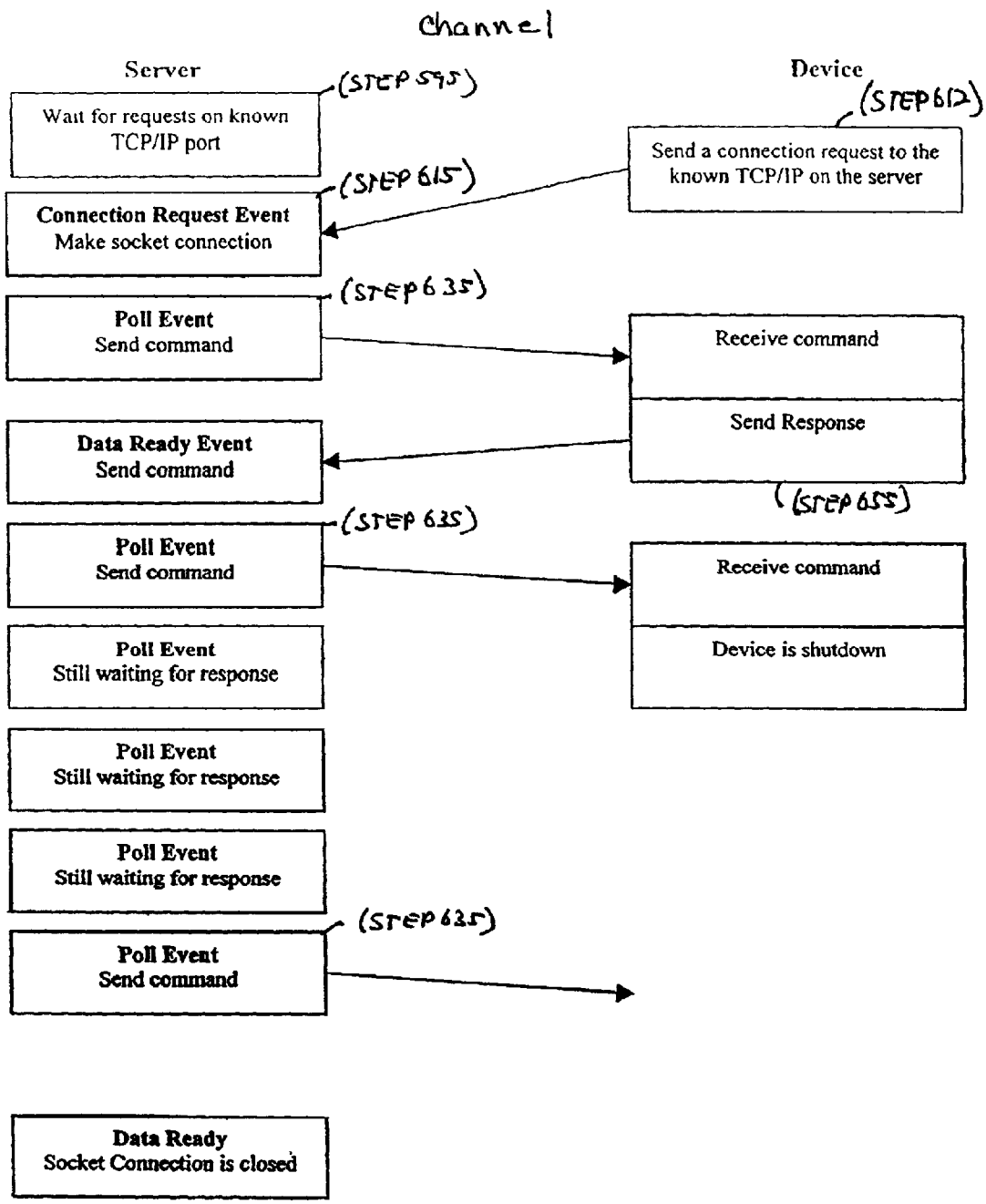
Figure 9 Pollster Socket Connection Timeline

FIG. 10

500 - Device Data Table - Data includes Just_Changed_flag 509
    502 - Latest device data table
    504 - Device snapshot data table
    506 - Trending data table
    508 - Setting and alarm change data table 510 - Device Configuration Table - institution information
    512 - History table 520 - Customization Table - control of display information
    522 - Group
    524 - Subgroup
    526 - Device type 530 - DeviceSpecific Table
    532 - Valued to be trended table
    534 - Description of alarm table

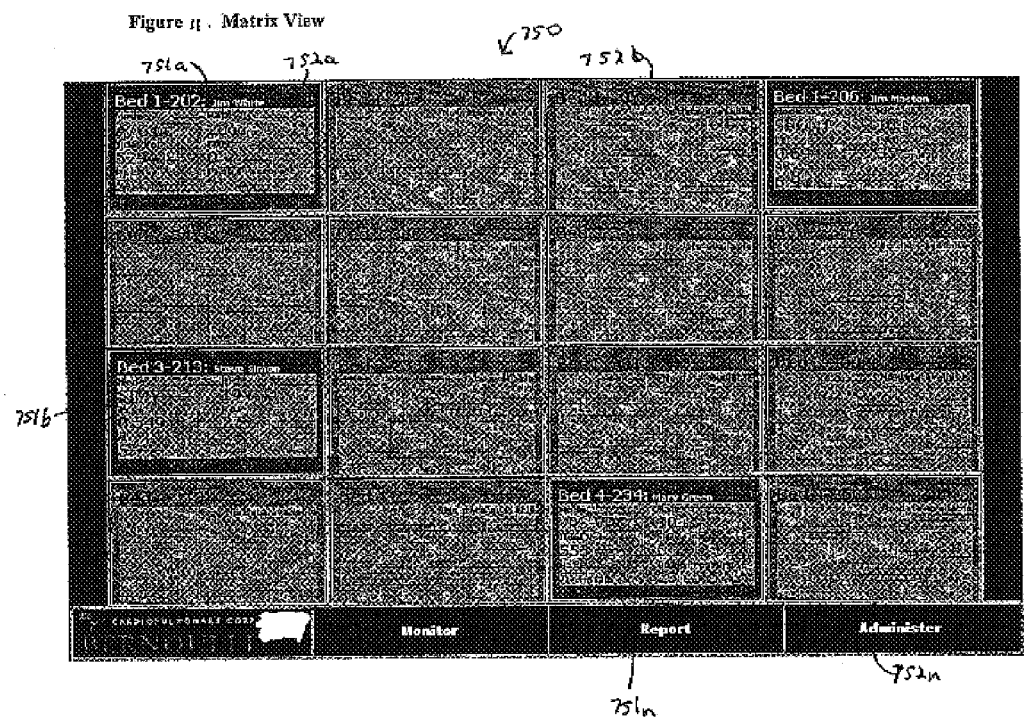
Figure 11. Matrix View

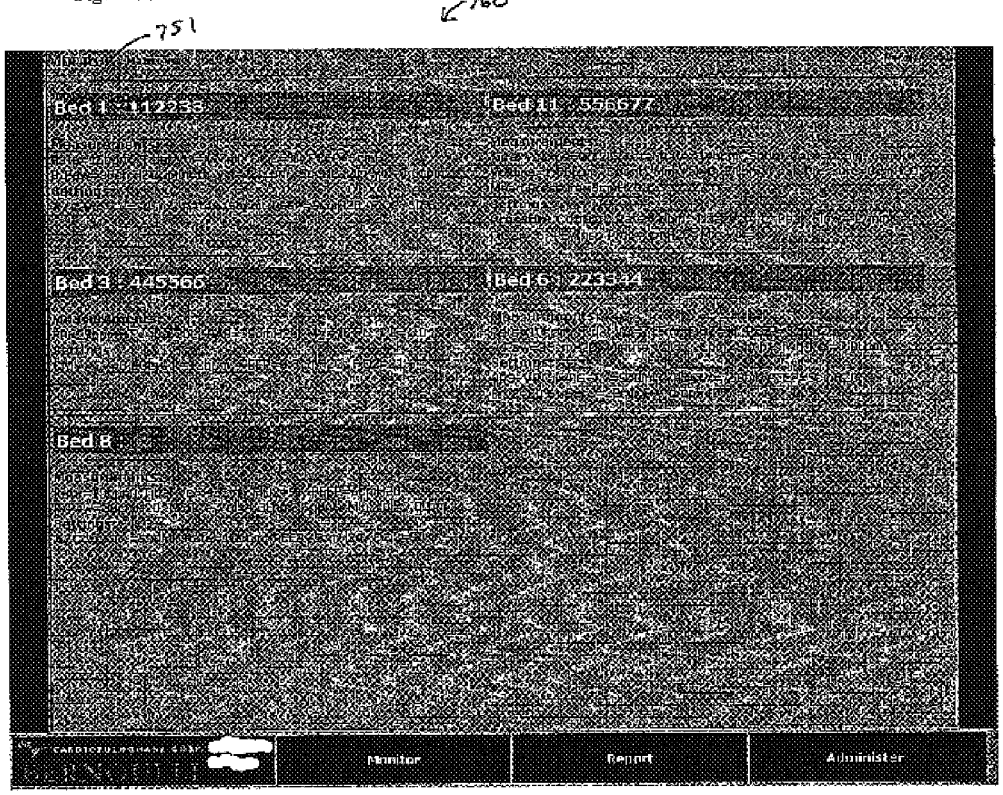
Figure 12. List View

Figure 13. Detail View  ↙770

| Settings VPS | Rate | Tidal Vol 500 | FiO2 50 | P/Paw --- | PEEP 5 | I-Time --- | Sensitivity 10ml |
|---|---|---|---|---|---|---|---|
| VPC | 12 bpm | 750 ml | 50 % | 24 cmH2O | 5 cmH2O | 0.8 sec | Pause Off |
| High Alarm --- Measures --- Low Alarm | 30 | 300 | | 25 | 5 | 0.4 | 100% O2 Off |
| | | | | | | | Apnea Settings P/Paw=10ml Rate=15bpm FiO2=50% |

| Mean Pressure 26cmH2O | I:E Ratio 1:2.9 | Compliance 24 | Resistance 16 | High Pressure Alarm Low I-Time Alarm |
|---|---|---|---|---|

NETWORK MONITORING SYSTEMS FOR MEDICAL DEVICES

TECHNICAL FIELD OF THE INVENTION

This invention relates in general to network monitoring systems for medical devices, more particularly, to network monitoring systems that collect data from heterogeneous devices for display at a central monitoring station.

BACKGROUND

Remote medical monitoring systems provide the advantage of monitoring a plurality of medical devices connected to one or more patients from a single site. In a health care facility, a single monitoring system station permits simultaneous monitoring and interaction with remote medical devices located, for example, in a patient's hospital room. Network monitoring systems provide uniform and continuous patient monitoring while reducing the numbers of trained health care personnel needed to monitor and interact with each medical device.

Remote monitoring systems having numerous disadvantages are currently used in health care facilities. These prior art systems typically require manual entry of data into the patient's record. Waveform data or similar data is typically generated from the network system as a hard copy and manually entered by cut and paste into the patient's medical record. Manual entry of data into a patient's medical record is likely to introduce transcription errors in the patient's medical record.

Some prior art monitoring systems are capable of monitoring devices of the same make and model manufactured by the same company. Typically, health care institutions purchase medical devices, such as ventilators, from a number of different manufacturers. As currently known in the field of respiratory ventilators, in order to monitor a ventilator from a remote location, a remote monitoring system is required for each ventilator make and model. Consequently, a monitoring station and additional personnel are required to monitor each ventilator type. As a result, efficiency that would otherwise be introduced by having a network monitoring system that monitors heterogeneous ventilators, is diminished.

SUMMARY OF THE INVENTION

The network monitoring system for medical devices according to the invention monitors and collects data, such as medical device settings, measured patient values, alarm conditions, and other data, from heterogeneous devices and displays the data at a central monitoring station. The display of collected data uses web technology so that the data can be displayed on any client computer connectable to an institution's intranet. In a further embodiment of the invention, trending data of various patient parameters is gathered so that users can view the patient's recent history. A log is kept of the important events that occur on the medical device and of important patient parameters to provide diagnostic information to caregivers such as nurses, technicians, and physicians.

In one embodiment of the invention, each medical device has its own data acquisition service application on a server that either listens for unsolicited data or actively polls data from the medical device. These applications are optimized to collect data and load it into the database quickly. In one embodiment of the invention, the medical device is a ventilator.

The database, in one embodiment, is Open Database Connectivity (ODBC) compliant so that the database is accessible to the server side web pages. The server side web page provides tables that store device data, configuration data, customization data and device-specific data. Queries made to the database in one embodiment are stored to speed up complicated query functions such as table joins.

In one embodiment of the invention, the data obtained by the data acquisition service application on the server is displayed by a web browser or a client connected or connectable to a hospital intranet. Web pages are generated by executing code on the server using data stored in the database and outputs standard HTML.

BRIEF DESCRIPTION OF THE DRAWINGS

FIG. 4 is a flow chart of one embodiment of the operation of the listener application of FIG. 3 according to the invention.

FIG. 5 is a flow chart of one embodiment of the operation of the load thread application of FIG. 3 according to the invention.

FIG. 6 is a flow chart of the operation of an embodiment of a parser according to one embodiment of the invention.

FIG. 7 is a diagram of a pollster application according to one embodiment of the invention.

FIG. 8 is a flow chart of the operation of one embodiment of the pollster application of FIG. 7 according to one embodiment of the invention.

FIG. 9 is a flow chart of one embodiment of a connection request event according to the invention.

FIG. 10 illustrates embodiments of data tables according to the invention.

FIG. 11 illustrates a Matrix View screen display according to one embodiment of the invention.

FIG. 12 illustrates a List View screen display according to one embodiment of the invention.

FIG. 13 illustrates a Detail View screen display according to one embodiment of the invention.

DETAILED DESCRIPTION OF THE INVENTION

Figure 1:
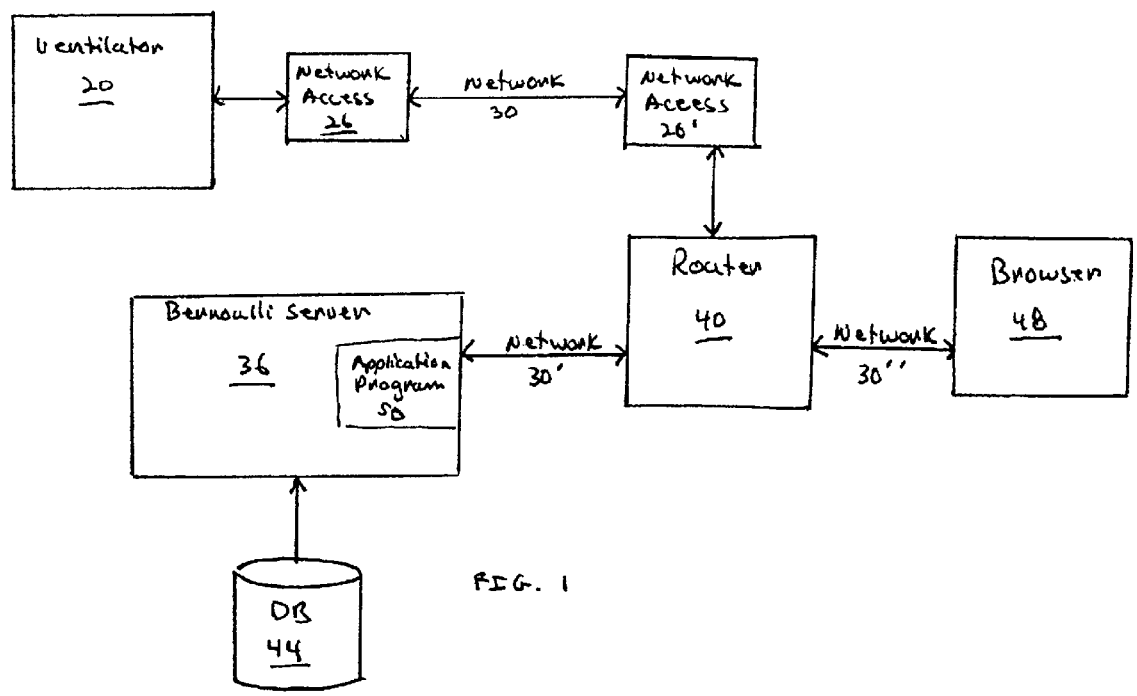
FIG. 1 is a block diagram of an embodiment of the invention.

In brief overview and referring to FIG. 1, a system constructed in accordance with the invention includes a medical device 20 such as a ventilator, connected to a network access device 26 such as a wireless transceiver. The network access device 26 communicates with a network 30 such as a 802.11 wireless Ethernet® local area network. A server 36, such as the Bernoulli server manufactured by the Cardiopulmonary Corporation Milford, Connecticut, executing an application program 50 is also in communication with the network 30 through a network access point 26' through a router 40 by way of a network 30' which may be but need not be the same as network 30. The server 36 communicates with a database 44 and a user accesses information on the server 36 using a browser 48 on a client computer through a network link 30" which again may be the same as, but need not be the same as networks 30, 30'.

In operation, the Bernoulli server 36 requests information from the medical ventilator 20 generally through the router 40. Data obtained from the medical ventilator 20 is stored in the database 44. When a user wishes to access ventilator data from the medical ventilator 20, the user uses a browser 48 to read the ventilator files stored in the database 44.

Figure 2:
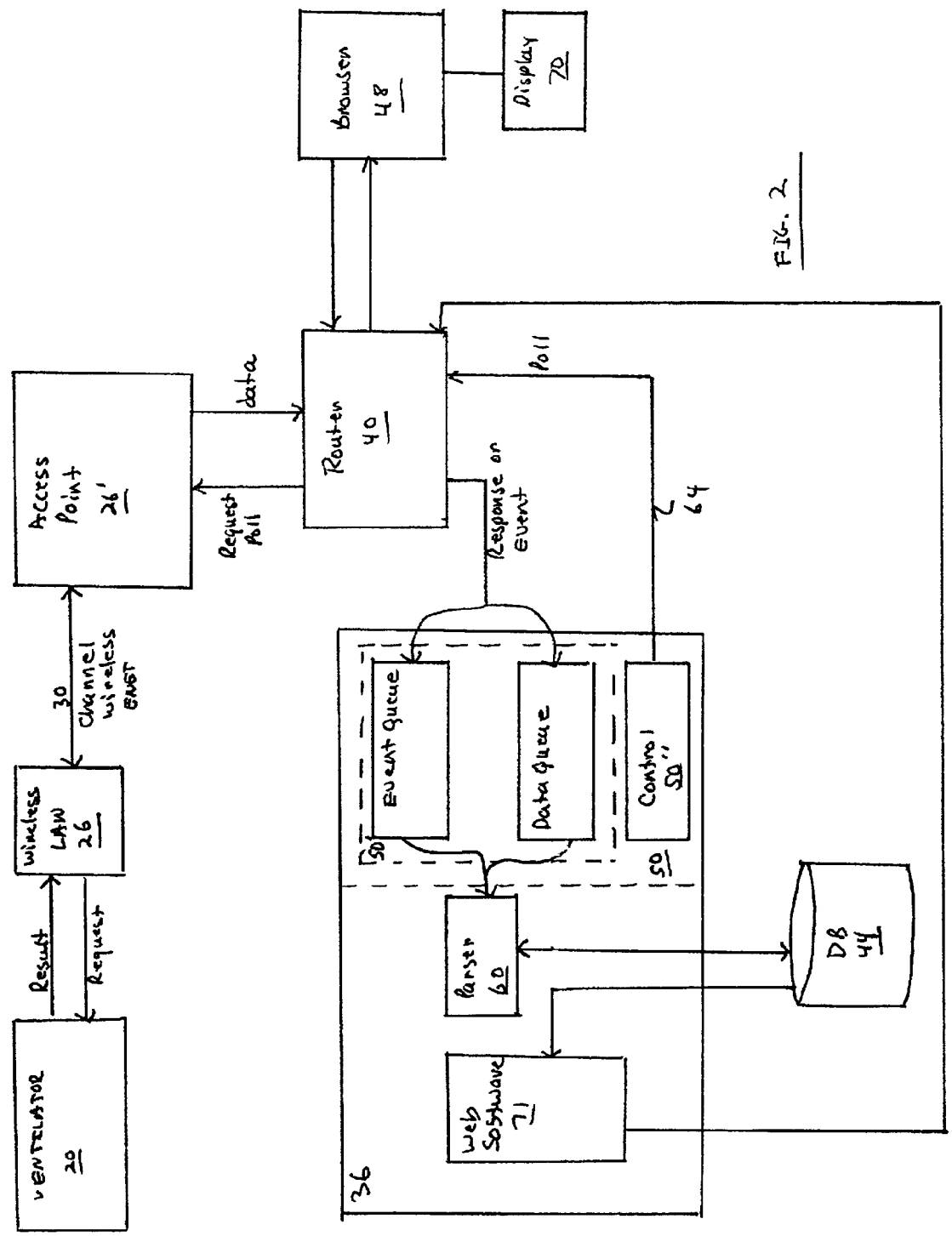
FIG. 2 is a more detailed block diagram of the embodiment of the invention shown in FIG. 1.

In more detail and referring also to FIG. 2, in one embodiment the medical ventilator 20 is connected, via an RS232 serial port, to a network access point 26. The network access point 26 converts the serial RS232 data available from the medical device 20 to a TCP/IP protocol for transmission over the network 30. In one embodiment, the network access device 26 converts the serial data to Ethernet data and sends the Ethernet data to an Ethernet hub for transmission to the server 36.

In another embodiment of the invention, the network access device 26 is a wireless Ethernet transceiver which not only converts the serial RS232 data to the correct protocol for a wireless Ethernet network but also converts the data to radio frequency data which is then broadcast generally over a limited area. The radio frequency data is received by a wireless network access point 26' which converts the radio frequency data back to TCP/IP data on a network connection and sends the data to the appropriate data acquisition application 50 on the server 36. Conversely, the network access point 26' also converts data from the server 36 to a wireless TCP/IP protocol which is transmitted via the wireless network 30 and received by the network access device 26. The network access device 26 then converts the received radio frequency information to serial RS232 data for use by the medical ventilator 20.

According to the invention, a dedicated data acquisition application 50 on the server 36 is used for each medical ventilator type 20. That is, generally each brand of ventilator will have its own protocol and will have a separate application program 50. Each data acquisition application 50 is in part a listener program 50' specifically programmed to communicate with the medical ventilator type 20. Data acquisition applications 50 that send commands to prompt for data include what are referred to as pollsters 50". Since the listener application 50' and the pollster application 50" typically are running, in one embodiment they are written as a service application.

Figure 3:
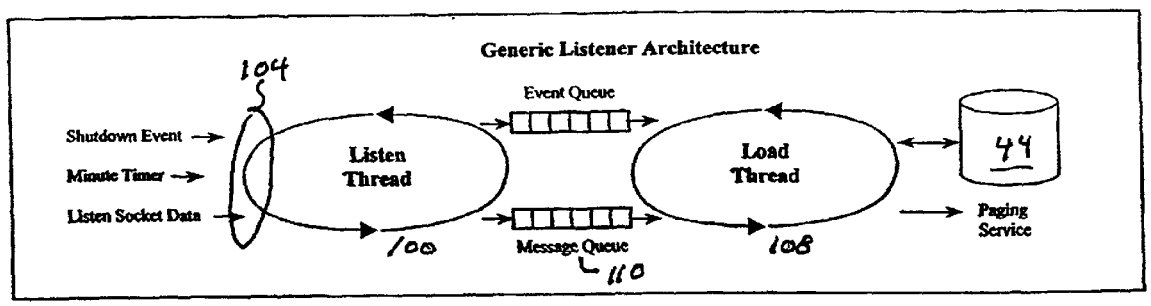
FIG. 3 is a diagram of a listener application according to one embodiment of the invention.

In one embodiment, according to the invention, referring to FIG. 3, a listener application 50' listens for data at a known User datagram protocol/Internet protocol (UDP/IP) port. The UDP protocol allows the data to go in one direction from the medical device 20 to the server 36 without the need for an established socket connection. In another embodiment, the time spent listening by the listener application 50' on the known UDP/IP port is maximized by using a multithread program execution approach. Referring to FIG. 3, for this embodiment, two threads are utilized: a listen thread 100 waits for data on the network access port 104 and a load thread 108 processes the received data and stores it in the database 44.

In this embodiment, referring to FIG. 4, the listen thread waits in STEP 300 for one of three events to occur. The three events are the shutdown event (STEP 310), the data ready event (listen for socket data) (STEP 320), or the minute timer event (STEP 330). The shutdown event (STEP 310) is triggered when the service Application Protocol Interface (API) requests to shutdown the listener application (STEP 340). The data ready event (STEP 320) is triggered when data is available on the UDP/IP network port so that data can be read (STEP 350) and put into a message queue (STEP 360).

The minute timer event (STEP 330) is unlike the other two events in that it is a periodic event triggered once per minute. Each time the minute timer is triggered, the current values or the configured parameters that are set for the ventilators 20 are appended to a table of data (STEP 370), the trend data table, described below, with a time stamp. Any trend data older than a configured time (for example, a default of 72 hours) is purged from the trend data table (STEP 380). Also any medical ventilator data in the active device data table described below older than two minutes is purged to prevent possible user misinterpretation of the data. In a particular embodiment of the invention, each time the minute timer is triggered, there is a check to see if it is time for a scheduled "snapshot" of the active data to be recorded. A "snapshot" is the action of copying all of a medical device's data from the active data table and placing it into a snapshot table, described below, with a time stamp. Snapshots are used to track the medical device state at the time of important events (STEP 400) for reporting purposes.

Referring also to FIG. 5, according to the invention, once the listen thread 100 receives data, the load thread 108 waits for the data to arrive in the message queue (STEP 410). Once the data has been received in the message queue, all values are analyzed from the data (STEP 420) and the name of the value is determined (STEP 430) If the value exists (STEP 440), and has not changed (STEP 460), no changes are made and the loop is continued. If the value does not exist (STEP 400), a value is created (STEP 450) and the loop is continued. If the value has changed (STEP 460), the value is updated for the device (STEP 470) and the loop is continued. After all of the values have been processed then STEP 420 makes adjustments to the data. If a setting was changed on the ventilator or an alarm was triggered (STEP 490), all active data is transferred to the snapshot table with a timestamp (STEP 500). In one embodiment, an alert is sent by Simple Mail Transport Protocol (SMTP) or telephony (STEP 521) to a remote device such as a pager. After all processing is finished, the Just_Changed flags are cleared (STEP 531).

In more detail once the message is received by the listen thread, the individual medical ventilator values are parsed out of the data stream by the parser 60 (FIG. 2). Referring also to FIG. 6, in one embodiment, for example, data received from the medical ventilator 20 (STEP 415) includes a single line with four ASCII values separated by spaces and terminated with a carriage return ("500 020 030 004"). The name of each value is determined (STEP 600; STEP 601; STEP 602; STEP 603;) by using the data protocol of the medical ventilator, for loading into the active data table of the database 44.

The data response may contain for example, tidal volume, oxygen setting, a high pressure limit and an inspiration time and may be associated with the following database names: chTV, stFIO2, stPPAWhi, stITIME. The database names and the medical device identification, for example, DevA, are used as keys in the active data table described below. According to this embodiment of the invention, the first row to be added to the database in the active data table (STEP 650) in the above example is: DevA, chTV, 500. A new row is created in the active data table for the device value if the device value does not already exist (STEP 440). No changes are made if the device value is the same as the one already in the table. The device value is only updated (STEP 470) if it is different than the value already in the table (STEP 460).

Any adjustments (STEP 480) to the device 20 that need to be made are done once all the data has been parsed and loaded. Examples of adjustments (STEP 480) include scaling the inspiration time down to hundredths of seconds. If the adjustment requires checking the values of multiple parameters, a temporary device value name may be used when loading this data. The adjustment process stores the value into the final device data name to avoid flickering in the displays. For example, the adjustment process might load the inspiration time value of 004 with the temporary name of sxITIME during the loading process (STEP 603), check the ventilation mode value (STEP 604), and if Mode= Pressure, then save the value of 0.04 with the stITIME name during the adjustment process (STEP 605).

According to one embodiment of the invention, the monitoring application 50 can request that data be sent by the ventilator 20 using a pollster application or pollster portion 50" of the device application 50. The pollster application 50" sends commands 64 to the medical device 20 over TCP/IP socket connections to elicit data responses. The socket connections are tracked in a connection list so that the connection can be held open from command to command. The pollster application waits for connection request at a predefined or well known TCP/IP port. When the medical device 20 sends a connection request to that port, the pollster application 50" makes the connection by way of another random port using the standard TCP/IP "accept" functionality.

In one embodiment of this application, referring to FIG. 7, the dual thread approach is also used. A polling thread and a load thread are executing in the pollster application 50". Referring to FIG. 8, in one embodiment of the invention, the polling thread waits (STEP 600) for one of five events to occur. The first three of the five events are the same as in the listen thread described above: the shutdown event, data ready event (listen socket data), and minute timer event.

In this embodiment, referring to FIG. 8, the polling thread waits in STEP 600 for one of the five events to occur. The shut down event (STEP 610) is triggered, like in the listen thread described above, when the service applications protocol interface (API) requests to shutdown the polling application (STEP 640). The data ready event (STEP 620) is triggered either when data to be read is available on the UDP/IP port or when there is notification that the socket connection has been broken (STEP 627). When data is available to be read (STEP 650), the data is appended to the message queue (STEP 660).

The minute timer event (STEP 630) is a periodic event triggered once per minute. Each time the minute timer is triggered, the current values or the unfigured parameters are appended to a table of data (STEP 670), the trend data table described below, with a time stamp. Any trend data older than a configured time (for example, default of 72 hours) is purged from the trend data table (STEP 680). Also any device data in the active device data table, described below, older than two minutes is purged to prevent possible user misinterpretation of the data. In a particular embodiment of the invention, each time the minute timer is triggered, there is a check to determine if it is time for a scheduled "snapshot" of the active data to be recorded (STEP 690). Snapshots are used to track the medical ventilator state at the time of imported events (STEP 700) for reporting purposes.

Referring also to FIG. 9, in addition, the polling thread 400 also waits (STEP 595) for a connection request event (STEP 615) (connect socket data) and a polling event (polling timer) (STEP 635). The connection request event (STEP 615) is triggered when a medical ventilator 20 requests a socket connection using the well known TCP/IP Port for this specific application 50" (STEP 612). The connection, once made, is stored in a connection list. A new entry is made in a device list table in the database 44 the first time that a response is received by the application program 50 from a ventilator. The medical ventilator's IP address is used to create a unique medical device identification in the table. Commands or polls are sent to each established connection once per second (STEP 635).

The polling event is triggered ten times a second so that commands (polls) can be spaced apart in a random pattern to reduce the possibility that many requests will be sent by the various application programs at the same time thereby interfering with access to the network. Commands are not sent if the data response from the device (STEP 655) has not been received from the last command sent. The connection stops waiting after three such missed poll events and then is closed.

Referring now to FIG. 10, in more detail, there are four different types of tables in the database: Device Data Tables 500, Device Configuration Tables 510, Customization Tables 520, and DeviceSpecific Tables 530. The Device Data tables 500 hold data acquired from the medical devices 20. There are tables for holding the latest device values 502, device snapshot information 504, trending data 506, and a record of setting changes and alarm events 508. A Just_ Changed_flag 509 is set (STEP 531) within the table row when data is updated in the device data table. This flag 509 allows queries to determine if either a setting has just changed or alarm condition has just occurred. When one of these conditions is met, a snapshot of the active data is saved into the snapshot table 504 (STEPS 400 or 700, FIGS. 4 and 8, respectively). A new entry is appended to the log of events table 508 marking this event. Remote alerts can be sent (STEP 521) to numeric or alphanumeric pagers when specific alarms occur. The alarming medical ventilator 20 is associated with a patient and the patient is associated with a pagee before a remote alert can be sent. The Just_ Changed_flag 509 is cleared (STEP 531) for all the active device data after all of the checks have been made.

The Device Configuration tables 510 store the information about the institution like the list of beds, patients, users, etc. The history 512 of the mappings of devices, beds, and patients is stored in the configuration table. This table is important when recovering patient information after changes have been made. The Customization tables 520 hold information that controls the appearance of most of the user interface. All customizations are stored together to facilitate future expansion of the system. Customizations are organized by Group 522, Subgroup 524, and DeviceType 526. The customizations are stored in fields that have generic names (Param1, Param2 . . . ) so the database form used to enter the data must operate in conjunction with the web page that runs the query in order to correctly interpret the values. The DeviceSpecific tables 530 store information specific to a medical device type used for data acquisition. There are tables to mark the values that are to be trended 532 and tables to hold the descriptions of alarms, settings, and measured values 534.

Data is extracted from the database 44 using Queries. Queries have been developed to speed the cases where these tables must be joined to access the data. For example, there is a query that combines the header information in the Snapshot table with the data in the Snapshot Data table. Queries are also used to hold business rules like determining when to take a snapshot because an alarm condition has just occurred. There are some stored procedures, or action queries depending on the database technology, used to manage the TrendData table.

Queries are made to the system through the web software 71. In one embodiment, for example, there are three main parts of the user interface 70: Monitoring, Reporting, and Administration. These functions are displayed as 'Monitor', 'Report', and 'Administer' buttons, respectively, at the bottom right side of the screen. The Monitor screen, for example, is arranged to allow the user to view information on all patient beds, or groups of patient beds, simultaneously, with the option to view more detailed information on any individual patient bed. The Monitor screen provides information such as patient settings, measured values, and alarm values. The Report screen, for example, allows the user to choose from Trends, Log of Events, Snapshots, etc. to view. After one of these reports is chosen, the user is taken through a series of screens to set up the parameters necessary to see the specified report. The Administration screen, for example, allows the user to add, remove, or change the status of patients and medical devices on the network.

In more detail, three different views are available to the user through the Monitor screen: the matrix view 750, the list view 760, and the details view 770. Referring to FIG. 11, in one embodiment Matrix View screen 750 is primarily used at a central monitoring station. This screen 750 is filled with a matrix displaying the status of all configured beds 751a–751n, generally 751, including beds without assigned patients. The number of columns in this matrix may be adjusted for optimal viewing. In one embodiment, no more than twenty beds 751 are displayed on the screen 750 at once. If there are more configured beds 751 than can fit on the screen, then tabs (not shown) will appear on the screen to select from configured groups of beds; e.g., view all of the NICU beds, SICU beds, or Step Down beds. In one embodiment, the user interface 70 is a web page.

Each bed 751 is displayed in its own web frame cell 752a–752n (generally 752) with a border, and parameter settings are displayed if there is an assigned patient and medical ventilator. In one embodiment, the displayed information as well as the border color is medical ventilator dependent. The server side code looks in the customization tables 520 for information about which device data to display for the assigned medical ventilator. This information includes for example, titles, units, and most importantly the data name in the vent data table. The device data is then looked up in the vent data table, combined with the title and units, and then sent to the client web browser 48. In a particular embodiment, if there is an alarm condition on the device, the border will change to bright red and the text of the alarm will be displayed. In a further embodiment, if the alarms have not been silenced on the device, an audible alarm will sound. The contents of each bed web frame 752 are refreshed every two seconds.

Whereas the matrix view web page 750 with its multiple frames and frequent refreshes requires more bandwidth than is commonly available over dialup lines, the list view web page 760, illustrated in FIG. 12, is optimized for slow connections. In one embodiment, the list view page 760 has a single frame displaying information only about the active beds 751. Much more information is displayed for each bed 751 in the list view 760 as compared to the matrix view 750, which reduces the need to go to the details view 770. The user is able to display a more detailed view by clicking on the bed title, which splits the screen in the same way as the matrix view.

If the user clicks anywhere within a web frame cell 752 on the matrix view web page 760, i.e. selects a patient bed 751, then a web page 760 with two different sections will appear. In one embodiment, the top section of the screen will display a small version of the matrix view web page 750 while the bottom section will display detailed information about the selected bed.

The detailed view web page 770, illustrated in FIG. 13, for example, is divided into five different sections: title, settings, simple settings, other measurements, and alarms. The title section identifies the bed and patient and has the ability to send an alert to a remote user, allow the user to view this detail section 770 as a full screen, or to print the page.

In one embodiment of the detailed view 770, the settings section is generally set up as a table with five rows: Primary Setting, Secondary Setting (if supported by the medical device), High Alarm Limit, Measurement, Low Alarm Limit. Each primary setting is labeled with a title and units. If the medical device has dual modes, then the secondary settings are displayed below the primary settings. Each column shows information about one setting with any related measured value and alarm limit. The alarms and measurements are displayed proportionally to the maximum setting value. If the measured value is outside the alarm limit, then the alarm background will be highlighted in red to draw attention to it. Three rows will be used if there is no maximum value set for the setting and no secondary settings.

The simple settings section displays those settings that have no related alarm limits or measured values. Also included in this section is a summary wrap-up of the apnea settings when displaying data from a ventilator device 20. The Other Measurements section displays those measured values that have no related alarm limits or settings. The Alarms section displays the current medical device alarm conditions.

Information may be accessed as a report. The reporting system provides the maximum amount of flexibility for adding, modifying, and removing individual reports. Reports are web pages that may require a number of parameters such as the patient identification. The customization tables in the database are used extensively to store navigational information. The starting screen of the report navigation is the list of available reports obtained from the database; e.g., Snapshots, Flowsheets, Trends, Log of Events, and Log of Remote Alerts. The user is always able to get back to this starting screen by clicking on the Begin button on the top of the screen.

The customization table holds the order of report parameter web pages for each report. When the user selects a report, the server side uses the customization table to determine to display either one of the report parameter web pages or the report web page itself. These pages allow the user to specify the value of a parameter such as patient, bed, or time range. So if the report is only for an individual patient, the patient parameter page will display only the list of patients with their assigned beds that have data for the report. The time range parameter page sets both a start and end time defaulting to the last twelve hours of data. All times are to be bounded by date range in the data itself. The user is able to directly enter dates by typing on the keyboard or click on a set of buttons to adjust by day, hour or minute. There are buttons to go back to the "last" twelve hours, move the range twelve hours ahead or behind. Other parameter pages may be developed specifically for a given report. The value of each parameter is stored as a session variable on the server. The session variable also stores the value of current "step" in the order of parameters. The current step is decremented when the user clicks on the Back button and the appropriate parameter page is displayed.

Although the reporting system is built to be extensible, there are a few reports considered to be standard. The Snapshot report shows a detailed summary of the state of a medical ventilator 20 at the time of a triggering event. The user must first select a patient. Then a time range is used to create a filtered list of snapshot reports for the patient. The user then chooses from this list to display all of the measured values, settings, and alarms at the time of the snapshot.

The Event Log report displays all of the important events that have occurred for a patient over a specified time frame. The user first must select a patient and time range for the report. Then there are several specific options for snapshot reports including different event filters, report pagination and sort order. Finally the report is displayed detailing all of the setting changes, alarm conditions and clinician interventions.

The Trend report is a graphical line chart showing the movement of measured values. The user first must select a patient and time range for the report. Then the report is displayed with a separate line chart for each trend parameter. The user can choose to magnify the size of individual trend parameter charts.

These reports process the raw collected data into diagnostic information using "smart" software. A series of institution-specific hierarchical alarms may be viewed for each patient, in which the most critical alarm is ranked first, followed by each alarm in order of importance. As an example, new alarms will be created that may not be present on the medical device. Such an example might consist of a high tidal volume alarm for a ventilator that does not have one built-in. Clinicians often compare parameters in the context of other parameters when making a clinical decision. This decision making process is encapsulated into a rules-based system with the collected clinical signs and key respiratory data as input and suggested decisions as output. The result is an indicator suggesting whether or not the patient is progressing towards the need for clinical intervention. These results will be combined together into a triage report ranking patients by their clinical progress.

The administration pages are used to manage the assignment of medical devices to beds with patients. This administration starts with the display of all current associations and the list of unassigned medical devices. The user will be able to click on a button to admit a patient, edit a patient, move a patient and medical device, disconnect a medical device, or swap a medical device. These actions require a number of steps where the user will make selections. The values of these selections are stored in session variables until it is possible to perform the action. The user will be able to cancel the action or move backwards by one step.

The user can choose to admit a patient. The user must provide the patient name along with an optional medical record number and comment. The user then selects the bed from the list of unassigned, available beds. The user selects the medical device from the list of unassigned medical devices. The patient, bed, and medical device are all assigned to each other after these selections have been made.

The user can choose to edit the information about a patient. The user must first select the patient to edit. Then the selected patient's information will be presented in an editable format. When the user finishes, the changes will be made.

The user can choose to dissociate the patient from the bed, where the patient may remain in the bed but is no longer connected to the medical device. Once the user selects the patient, the patient will be unassigned from the bed and medical device. This association is remembered in the database. The institution can elect to purge the data tables for this association from the database at this point or move them into an archive database.

The user can choose to move the patient to another bed. The user first selects the patient to be moved from a list of assigned beds. Then the destination bed is chosen from the list of unassigned beds. The user can also choose to swap a currently assigned medical device with an unassigned medical device. This may be necessary when preventative maintenance is performed. The user first selects the patient to move from a list of assigned beds. Then an unassigned medical device is selected from the list of unassigned medical devices.

Requiring the user to log on before sensitive data is displayed on the web pages insures patient confidentiality. There is an option button to increase the level of data access in the administration section. A log on screen is displayed when the user requests a high data access level for the current web session. The logon screen requires certain information from the user in order to obtain patient information.

A set of monitoring pages are available specially formatted for viewing on web browsers of handheld mobile devices. The main requirement is that these mobile devices have small displays with tall aspect ratios. The user will be able to display a modified list view.

There are cases when a clinician signature is required to validate that the snapshot data shown on the handheld mobile device was compared to the data displayed on the medical device 20. This requires a clinician to be in possession of a handheld mobile device and be physically present at a patient's bedside. There are special screens on the handheld mobile device that may be viewed only by logged on users. These screens on the handheld mobile device display the device data to the user who then directly compares this data to that on the medical device. If everything matches, then the user can initiate a manual snapshot of the data which includes their signoff signature.

All of the data from the medical devices connected to a patient acquired by the network monitoring system and reports can be stored electronically as part of the patient's medical record. Alternatively, a hard-copy printout of the data can be included with the patient's permanent medical record.

While the present invention has been described in terms of certain exemplary preferred embodiments, it will be readily understood and appreciated by one of ordinary skill in the art that it is not so limited, and that many additions, deletions and modifications to the preferred embodiments may be made within the scope of the invention as hereafter claimed. Accordingly, the scope of the invention is limited only by the scope of the appended claims.

What is claimed is:

1. A ventilator monitoring system comprising:
   a plurality of ventilators, wherein at least two of said ventilators are heterogeneous types, said ventilators having data;
   a first network access point in communication with one of said plurality of ventilators, said first network access point passing requests to and receiving data from said one of said plurality of ventilators;
   a network in communication with said first network access point;
   a second network access point in communication with said network;
   a server in communication with said second network access point, said server comprising:
      a dedicated ventilator application program for each type of heterogeneous ventilators; and
      a listener/pollster;
   a database in communication with said server, said database comprising data from said plurality of ventilators; and a browser in communication with said server;

wherein said listener/pollster transmits requests to and receives data from said plurality of ventilators through said second data access point and passes requests to and data from said dedicated ventilator application program, wherein said dedicator ventilator application passes data to and receives data from said database, and wherein said browser receives data from said server and displays data to a user.

2. The system of claim 1 wherein said network is a wireless Ethernet network.

3. The system of claim 1 wherein said data received by said browser comprises standard HTML output.

4. The system of claim 1 wherein said ventilator communicates with said network access point by way of an RS232 connection.

5. The system of claim 1 wherein the protocol of the network is TCP/IP.

6. The system of claim 1 wherein said data comprises ventilator settings.

7. The system of claim 1 wherein said data comprises patient values measured by said ventilator.

8. The system of claim 1 wherein said data comprises alarm conditions detected by said ventilator.

9. The system of claim 1 further comprising a router in communication between said server and said second network access point.

10. The system of claim 1 wherein the listener/pollster comprise a plurality of threads.

11. The system of claim 10 wherein said plurality of threads comprise a receive thread and a load thread.

12. The system of claim 1 wherein said browser communicates with said server by way of said network.

13. A ventilator monitoring system comprising:

a plurality of ventilator means, wherein at least two of said ventilator means are heterogeneous types, said ventilator means having data;

first network access means for communicating with one of said plurality of ventilator means, said first network access means passing requests to and receiving data from said one of said plurality of ventilator means;

network means for communicating with said first network access means;

second network access means for communicating with said network means;

server means for communicating with said second network access means, said server means comprising:

a dedicated ventilator application means for each type of heterogeneous ventilator means; and a listener/pollster means for transmitting requests to and receiving data from said plurality of ventilator means through said second data access means and for passing requests to and data from said dedicated ventilator application means;

database means for passing data to and receiving data from said server means and for storing data from said plurality of ventilator means; and browser means for receiving data from said server means and for displaying data to a user.

14. A method for monitoring a plurality of patients comprising:

providing a plurality of ventilators, wherein at least two of said ventilators are heterogeneous types;

collecting data from said plurality of ventilators via a dedicated ventilator application for each of said ventilator types;

transmitting said data via a network to a server said server comprising a dedicated ventilator application program for each type of heterogeneous ventilator, and a listener/pollster, storing said data in a database; and displaying said data on a web browser.

15. The method of claim 14 wherein said step of displaying said data comprises the steps of generating HTML output from said data and reading said HTML output with said web browser.

16. The method of claim 14 wherein said step of displaying data further comprises customizing said data according to data trends.

* * * * *